United States Patent [19]
Petersen et al.

[11] 3,931,220
[45] Jan. 6, 1976

[54] β-PHENYL-β-AZOLYL-NITROETHANES

[75] Inventors: Uwe Petersen, Cologne; Siegfried Petersen; Hans Scheinpflug, both of Leverkusen; Brigitte Hamburger, Cologne, all of Germany

[73] Assignee: Bayer Aktiengesellschaft, Leverkusen, Germany

[22] Filed: Nov. 30, 1973

[21] Appl. No.: 420,496

[30] Foreign Application Priority Data
Dec. 12, 1972  Germany............................ 2260704

[52] U.S. Cl. ...... 260/310 R; 260/308 R; 260/308 B; 260/308 A; 260/309; 260/309.2; 260/310 C; 424/269; 424/273
[51] Int. Cl.²......................................... C07D 231/12
[58] Field of Search ..................... 260/310 R, 310 C

[56] References Cited
UNITED STATES PATENTS

| | | | |
|---|---|---|---|
| 3,682,956 | 8/1972 | Howarth et al. ................ | 260/310 R |
| 3,714,182 | 1/1973 | Bandurco et al................ | 260/310 R |

*Primary Examiner*—Donald B. Moyer
*Attorney, Agent, or Firm*—Burgess, Dinklage & Sprung

[57]  ABSTRACT

β-phenyl-β-azolyl-nitroethanes of the formula

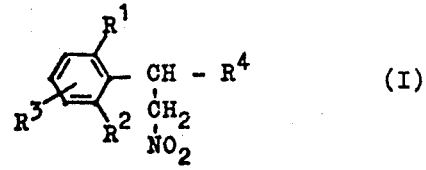

in which
R¹, R² and R³ each individually is hydrogen, lower alkyl optionally substituted by fluorine or chlorine, halogen, nitrile, thiocyano, nitro or alkoxycarbonyl with up to 6 carbon atoms in the alkoxy radical, and
R⁴ is a 5-membered heterocyclic structure with 1 to 4 nitrogen atoms which is bonded via nitrogen and which is optionally substituted by halogen, lower alkyl or alkenyl, —(CH₂)₄— or —CH=CH—CH=CH—,
which possess fungicidal and bactericidal properties.

4 Claims, No Drawings

β-PHENYL-β-AZOLYL-NITROETHANES

The present invention relates to and has for its objects the provision of particular new β-phenyl-β-azolyl-nitroethanes which may be substituted on the phenyl and/or heterocyclic ring and which possess fungicidal or bactericidal properties, active compositions in the form of mixtures of such compounds with solid and liquid dispersible carrier vehicles, and methods for producing such compounds and for using such compounds in a new way especially for combating pests, e.g., fungi and bacteria, with other and further objects becoming apparent from a study of the within specification and accompanying examples.

It has been disclosed in Chemie der Pflanzenschutz- und Schadlingsbekampfungsmittel (Chemistry of Plant Protection Agents and Pesticides), Volume 2, page 65, Heidelberg (1970), that compounds such as zinc ethylene-1, 2-bis-dithiocarbamate (Compound A) or sodium pentachlorophenolate, possess fungicidal and bactericidal effects, respectively. However, they suffer from the disadvantage that if the amounts used are low, the effect is not completely adequate.

It has now been found that the new β-phenyl-β-azolyl-nitroethanes of the formula:

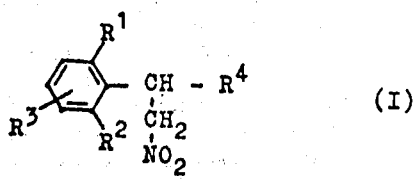

in which
R¹, R² and R³ each individually is hydrogen, lower alkyl optionally substituted by fluorine or chlorine, halogen, nitrile, thiocyano, nitro or alkoxycarbonyl with up to 6 carbon atoms in the alkoxy radical, and
R⁴ is a 5-membered heterocyclic structure with 1 to 4 nitrogen atoms which is bonded via nitrogen and which is optionally substituted by halogen, lower alkyl or alkenyl, —(CH₂)₄— or —CH=CH—CH=λ CH—, display strong fungicidal and bactericidal properties.

Surprisingly, the β-phenyl-β-azolyl-nitroethanes according to the invention display a considerably greater fungicidal and bactericidal effect than zinc ethylene-1,2-bis-dithiocarbamate or sodium pentachlorophenolate, which are known from the state of the art. The compounds according to the invention thus represent an enrichment of the art.

It has furthermore been found that the β-phenyl-β-azolyl-nitroethanes of the formula (I) are obtained by reacting ω-nitrostyrenes of the formula:

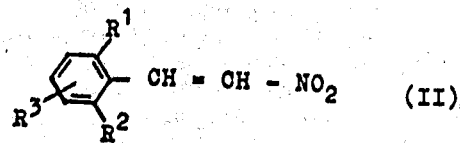

with nitrogen-containing heterocyclic compounds of the formula:
H — R⁴     (III)

optionally in the presence of inert solvents.

If 2,6-dichloro-ω-nitrostyrene and pyrazole are used as starting compounds, the course of the reaction can be represented by the following equation:

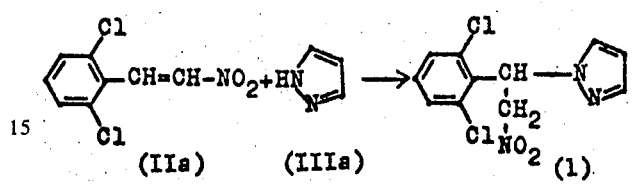

Preferably R¹, R² and R³ each independently is hydrogen, fluorine, chlorine, methoxycarbonyl, ethoxycarbonyl or optionally chlorinated or fluorinated methyl or ethyl radicals. R⁴ is a 5-membered heterocyclic structure with, preferably, 2 to 3 nitrogen atoms; as substituents, there may preferentially be mentioned: methyl, ethyl, chlorine, fluorine and the bifunctional groups —(CH₂)₄—or—CH=CH—CH=CH—. The ω-nitrostyrene starting materials of formula (II) which can be used according to the invention are disclosed in Houben-Weyl, "Methoden der organischen Chemie" (Methods of Organic Chemistry), Volume X/1, pages 330 et seq., Georg-Thieme-Verlag, Stuttgart (1971); as is known, they are prepared by condensation of aromatic aldehydes with nitromethane. The following examples may be mentioned: ω-nitrostyrene, 2-chloro-ω-nitrostyrene, 3-chloro-ω-nitrostyrene, 4-chloro-ω-nitrostyrene, 2,6-dichloro-ω-nitrostyrene, 2,4-dichloro-ω-nitrostyrene, 2,3,6-trichloro-ω-nitrostyrene, 2-bromo-ω-nitrostyrene, 2-fluoro-ω-nitrostyrene, 2-methyl-ω-nitrostyrene, 3-methyl-ω-nitrostyrene, 4-methyl-ω-nitrostyrene, 4-thiocyano -ω-nitrostyrene, 4-carbomethoxy-ω-nitrostyrene, 4-trifluoromethyl-ω-nitrostyrene, 2,ω-dinitrostyrene and 4,ω-dinitrostyrene.

The nitrogen-containing heterocyclic compounds of formula (III) which can be used according to the invention are also generally known. As examples there may be mentioned: pyrazole, 1,2,3-triazole, 1,2,4-triazole, benzotriazole, indazole, 4-chloropyrazole, 4-nitropyrazole, 3-chloro-1,2,4-triazole, 3,5-dimethyl-1,2,4-triazole, 4,5-dimethyl-1,2,3-triazole, 4,5,6, 7-tetrahydrobenzotriazole, 5-trifluoromethyl-indazole, 5-chloroindazole, 6-chloro-indazole, 5-bromo-indazole and 5-nitroindazole.

All inert organic solvents can be used as diluents. These preferentially include hydrocarbons, such as benzene and toluene, alkyl alcohols, such as methanol, ethanol and n- and i-propyl alcohol, ethers, such as dioxane and tetrahydrofurane and lower alkyl nitriles, such as acetonitrile and propionitrile. However, in many cases it is also possible advantageously to carry out the reaction without solvents by allowing the starting compounds to react with one another in the melt.

The reaction temperatures can be varied over a substantial range. In general, the reaction is carried out at between about 50°C and about 150°C, preferably between 70°C and 120°C.

The reaction can be carried out under normal pressure but also under elevated pressure. Preferably, it is carried out under normal pressure.

In carrying out the process according to the invention about 1 to 10 moles, preferably 1 to 5 moles, of the azole are employed per mole of the $\omega$-nitrostyrene. For working up, it is possible to distil off any diluent which may have been used and to extract excess or unreacted azole from the residue by means of water or a dilute mineral acid such as, for example, dilute hydrochloric acid or dilute sulfuric acid. The reaction product which remains undissolved can be purified according to conventional methods, such as, for example, by recrystallization from a suitable solvent, optionally in the presence of active charcoal, or by chromatography. The active compounds according to the invention are crystalline compounds and in some cases also nondistillable oils, the structure of which has been clarified by their elementary analysis and by infrared, nuclear resonance and mass spectra.

The active compounds according to the invention display a strong fungitoxic and bacteriotoxic action. They do not damage crop plants in the concentrations required for combating fungi and bacteria and have a low toxicity towards warm-blooded animals. They are suitable for use as plant protection agents and as agents for combating fungi and bacteria in protecting materials. Fungitoxic agents are employed for combating archimycetes, phycomycetes, ascomycetes, basidiomycetes and *Fungi imperfecti*.

The active compounds according to the invention have a very broad spectrum of action and can be used against parasitary fungi and bacteria which infect the parts of plants which are above ground or attack the plants through the soil, and against seed-borne pathogens.

The compounds according to the invention are active against fungi and bacteria which attack various crop plants, such as, for example, varieties of Pythium, varieties of Phytophthora, varieties of Fusarium, *Verticillium alboatrum*, *Phialophora cinerescens*, *Sclerotinia sclerotiorum*, varieties of Botrytis, *Cochliobolus miyabeanus*, *Mycosphaerella musicola*, *Cercospora personata*, *Helminthosporium gramineum*, varieties of Alternaria, varieties of Colletotrichum, *Venturia inaequalis*, varieties of Rhizoctonia, *Thielaviopsis basicola* and the bacterium *Xanthomonas oryzae*. The compounds according to the invention also act against diseases of cereals, such as, for example, *Puccinia recondita*, *Erysiphe graminis* and *Tilletia caries*.

The active compounds according to the invention additionally display an acaricidal action.

The active compounds according to the instant invention can be utilized, if desired, in the form of the usual formulations or compositions with conventional inert (i.e., plant compatible or herbicidally inert) pesticide diluents or extenders, i.e., diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g., conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g., benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g., petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g., glycol monomethyl ether, etc.), amines (e.g. ethanolamine, etc.), amides (e.g., dimethyl formamide, etc.), sulfoxides (e.g., dimethyl sulfoxide, etc.), acetonitrile, ketones (e.g., acetone, methyl ethyl ketone, methyl isobutyl ketone, cyclohexanone, etc.), and/or water; as well as inert dispersible finely divided solid carriers, such as ground natural minerals (e.g., kaolins, clays, alumina, silica, chalk, i.e., calcium carbonate, talc, attapulgite, montmorillonite, kieselguhr, etc.) and ground synthetic minerals (e.g., highly dispersed silicic acid, silicates, e.g., alkali silicates, etc.); whereas the following may be chiefly considered for use as conventional carrier vehicle assistants, e.g., surface-active agents, for this purpose: emulsifying agents, such as non-ionic and/or anionic emulsifying agents (e.g., polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, and acaricides, or insecticides, rodenticides, nematocides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well-known ultra-low-volume process with good success, i.e., by applying such compound if normally a liquid, or by applying a liquid composition containing the same, via very effective atomizing equipment, in finely divided form, e.g., average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g., about 20–100% by weight of the active compound.

Furthermore, the present invention contemplates methods of selectively killing, combating or controlling pests, e.g., fungi, bacteria and acarids, and more particularly methods of combating at least one of fungi and bacteria, which comprises applying to at least one of correspondingly (a) such fungi, (b) such bacteria, and (c) the corresponding habitat thereof, i.e., the locus to be protected, a correspondingly combative or toxic amount, i.e., fungicidally or bactericidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, gassing, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The synthesis, unexpected superiority and outstanding activity of the particular new compounds of the present invention are illustrated, without limitation, by the following examples:

EXAMPLE 1

Mycelium growth test

Nutrient medium used:
20 parts by weight of agar-agar
200 parts by weight of potato decoction
5 parts by weight of malt
15 parts by weight of dextrose
5 parts by weight of peptone
2 parts by weight of disodium hydrogen phosphate
0.3 part by weight of calcium nitrate
Ratio of solvent mixture to nutrient medium:
2 parts by weight of solvent mixture
100 parts by weight of agar nutrient medium
Composition of solvent mixture:
0.19 part by weight of acetone
0.01 part by weight of alkylaryl polyglycol ether emulsifier

| 1.80 parts by weight of water |
|---|
| 2    parts by weight of solvent mixture |

The amount of active compound required for the desired active compound concentration in the nutrient medium is mixed with the stated amount of the solvent mixture. The concentrate is thoroughly mixed, in the stated proportion, with the liquid nutrient medium which has been cooled to 42°C and is poured into Petri dishes of 9 cm diameter. Control plates without added preparation are also set up.

When the nutrient medium has cooled and solidified, the plates are inoculated with the varieties of fungi and bacterium indicated in the table and incubated in about 21°C.

Evaluation is carried out after 4 – 10 days, dependent on the speed of growth of the mycelium. When evaluation is carried out, the radial growth of the mycelium on the treated nutrient media is compared with the growth on the control nutrient medium. In rating the growth, the following characterizing numbers are used:
  1 no fungus growth
  up to 3 very strong inhibition of growth
  up to 5 medium inhibition of growth
  up to 7 slight inhibition of growth
  9 growth equal to that of the untreated control.

The active compounds, the active compound concentrations and the results can be seen from the table which follows:

Table 1

Mycelium growth test
Fungi and 1 bacterium

| Active compounds | Active compound concentration, ppm | Fusarium culmorum | Sclerotinia sclerotiorum | Fusarium nivale | Colletotrichum coffeanum | Rhizoctonia solani | Pythium ultimum | Cochliobolus miyabeanus | Botrytis cinerea | Verticillium alboatrum | Pyricularia oryzae | Phialophora cinerescens | Helminthosporium gramineum | Mycosphaerella musicola | Phytophthora cactorum | Venturia inaequalis | Pellicularia sasakii | Xanthomonas oryzae |
|---|---|---|---|---|---|---|---|---|---|---|---|---|---|---|---|---|---|---|
| $\begin{array}{c} \text{CH}_2\text{–NH–C–S} \\ | \quad\quad\quad\quad\;\text{Zn} \\ \text{CH}_2\text{–NH–C–S} \end{array}$ (with S above C) (known) (A) | 0 | 9 | 3 | 5 | 9 | 1 | 1 | 9 | 9 | 9 | 5 | 9 | 2 | 1 | 1 | 1 | 1 | 9 |

Table 1-continued
Mycelium growth test
Fungi and 1 bacterium

| Active compounds | Active compound concentration, ppm | Fusarium culmorum | Sclerotinia sclerotiorum | Fusarium nivale | Colletotrichum coffeanum | Rhizoctonia solani | Pythium ultimum | Cochliobolus miyabeanus | Botrytis cinerea | Verticillium alboatrum | Pyricularia oryzae | Phialophora cinerescens | Helminthosporium gramineum | Mycosphaerella musicola | Phytophthora cactorum | Venturia inaequalis | Pellicularia sasakii | Xanthomonas oryzae |
|---|---|---|---|---|---|---|---|---|---|---|---|---|---|---|---|---|---|---|
| (1) | 10 | 1 | 1 | 1 | 1 | 1 | 1 | 1 | 5 | 1 | 1 | 1 | 1 | 1 | 1 | 1 | 1 | 1 |
| (3) | 10 | 1 | 3 | 1 | 1 | 1 | 1 | 1 | 5 | 1 | 1 | 1 | 1 | 1 | 1 | 1 | 1 | – |
| (4) | 10 | 1 | 3 | 1 | 1 | 1 | 1 | 1 | 5 | 1 | 1 | 1 | 1 | 1 | 1 | 1 | 1 | 1 |
| (6) | 10 | 1 | – | 1 | 1 | 1 | 1 | 1 | 5 | 1 | 1 | – | 1 | 1 | 1 | 1 | 1 | 1 |
| (2) | 10 | 1 | 5 | 1 | 1 | 1 | 1 | 3 | 5 | 1 | 1 | 1 | 1 | 1 | 1 | 1 | 1 | 9 |
| (7) | 10 | 1 | 3 | 1 | 1 | 1 | 1 | 2 | 1 | 1 | 1 | 1 | 1 | 1 | 1 | 1 | 1 | 5 |
| (5) | 10 | 1 | 3 | 1 | 1 | 1 | 1 | 1 | 9 | 1 | 1 | 1 | 1 | 1 | 1 | 1 | 1 | 5 |
| (10) | 10 | 1 | 1 | 1 | 1 | 1 | 1 | 1 | 1 | 1 | 1 | 1 | 1 | 1 | 1 | 1 | 1 | 1 |
| (10) | 5 | 1 | 9 | 1 | 1 | 1 | 1 | 3 | 9 | 1 | 1 | 1 | 1 | 1 | 1 | 1 | 1 | 2 |
| (12) | 10 | 1 | 5 | 1 | 1 | 1 | 1 | 3 | 1 | 1 | 1 | 1 | 1 | 1 | 1 | 1 | 1 | 1 |
| (11) | 10 | 1 | 2 | 1 | 1 | 1 | 1 | 1 | 1 | 9 | 3 | 1 | 1 | 1 | 1 | 1 | 1 | 5 |

EXAMPLE 2

Microbicidal action / reciprocal germ inhibition values

The reciprocal germ inhibition values for some selected varieties from the three groups of bacteria, fungi and yeasts are listed in the table. These values indicate at what dilutions of the compounds mentioned the growth of the selected micro-organisms is completely inhibited when these compounds are added to an optimum nutrient medium for the organisms. The micro-organisms employed for this inhibition test occur widely and are known to be resistant towards conventional chemical preservatives and disinfectants.

The germ inhibition values listed are determined according to the customary dilution method, as follows:

The preparations to be tested are employed in various concentrations in the diluent mentioned. Known amounts of the previously dissolved preparations are introduced into the previously prepared test tubes filled with standardized nutrient substrates.

All work is carried out under sterile conditions. The various micro-organisms indicated in the table are incubated at 30°C.

The germ inhibition values indicated in the table show the concentrations which still suffice to prevent any growth.

Diluent: ethylene glycol.

Table 2

Microbicidal action/reciprocal germ inhibition values

| Active compounds | Aspergillus terreus | Trichophyton ment. | Candida albicans | Saccharomyces spec. | Bact. proteus | Staphylococcus aureus | Pseudomonas pyocyanea | Escherichia coli |
|---|---|---|---|---|---|---|---|---|
| 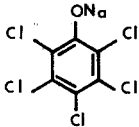 (known) (B) | 14,000 | | | | 3,000 | | 3,000 | 3,000 |
| 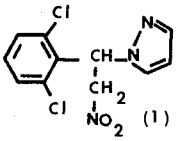 (1) | 55,000 | | | 55,000 | 11,000 | | | 11,000 |
| 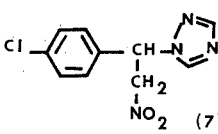 (7) | 35,000 | 75,000 | 75,000 | 35,000 | 3,400 | 3,400 | 7,100 | 7,100 |
| 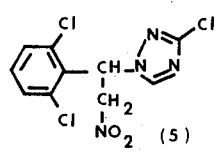 (5) | 72,000 | 72,000 | 72.000 | 72,000 | 3,000 | 3,000 | 7,200 | 7,200 |

The following examples illustrate the synthesis of the novel compounds;

EXAMPLE 3

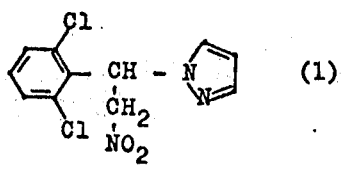 (1)

54.5 g of 2,6-dichloro-ω-nitrostyrene (0.25 mole) are mixed with 17 g of pyrazole (0.25 mole) and the mixture is fused for 3 hours at a temperature of 100°C. The melt which solidifies on cooling is recrystallized from petroleum ether. 55.2 g of β-(2,6-dichlorophenyl)-β-(pyrazolyl-1)-nitroethane of melting point 93° – 95.5°C are obtained. The yield of pure material is 77% of theory.

EXAMPLE 4

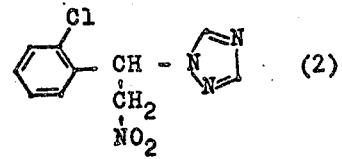 (2)

18.4 g of 2-chloro-ω-nitrostyrene (0.1 mole) in 100 ml of ethanol are kept, with 34 g of 1,2,4-triazole (0.5 mole), at a temperature of 70°C for 6 hours and the reaction mixture is then boiled up with active charcoal and filtered. The filtrate is then concentrated to about half its volume in vacuo, whereupon excess triazole precipitates. This is dissolved by adding about 500 ml of water and an undissolved somewhat smeary solid product which remains is isolated and recrystallized from ethanol. 18.4 g of β-(2-chlorophenyl)-β-(1,2,4-triazolyl-1)-nitroethane of melting point 85° – 87°C are obtained. The yield of pure material is 49% of theory.

The following compounds were prepared analogously:

Table 3

| Compound No. | Formula | Properties |
|---|---|---|
| 3 | [2,6-dichlorophenyl-CH(CH$_2$NO$_2$)-N(pyrazolyl-Cl)] | Melting point 98 – 100°C |
| 4 | [2,6-dichlorophenyl-CH(CH$_2$NO$_2$)-N(1,2,4-triazolyl)] | Melting point 103 – 105°C |
| 5 | [2,6-dichlorophenyl-CH(CH$_2$NO$_2$)-N(1,2,4-triazolyl-Cl)] | Melting point 114 – 116°C |
| 6 | [phenyl-CH(CH$_2$NO$_2$)-N(pyrazolyl)] | Oil<br>NMR (CDCl$_3$): δ 4.7 – 5.8 (8 lines); about 6.2 q; 6.29 q; 7.37 s; 7.46 d and 7.6 d |
| 7 | [4-chlorophenyl-CH(CH$_2$NO$_2$)-N(1,2,4-triazolyl)] | Melting point 91 – 93°C |
| 8 | [phenyl-CH(CH$_2$NO$_2$)-N(1,2,4-triazolyl)] | Oil<br>NMR (CDCl$_3$): δ 4.73 – 5.7 (8 lines); about 6.25 q; 7.35 s; 7.94 s and 8.18 s |
| 9 | [4-methylphenyl-CH(CH$_2$NO$_2$)-N(1,2,4-triazolyl)] | Oil<br>NMR (CDCl$_3$): δ 2.28 s; 4.72 – 5.7 (8 lines); about 6.2 q; 7.2 s; 7.95 s and 8.2 s |
| 10 | [2,6-dichlorophenyl-CH(CH$_2$NO$_2$)-N(pyrazolyl)] | Melting point 105 – 106°C |
| 11 | [2,6-dichlorophenyl-CH(CH$_2$NO$_2$)-N(4,5,6,7-tetrahydrobenzotriazolyl)] | Melting point 127 – 128°C<br>Analysis (C$_{14}$H$_{14}$Cl$_2$N$_4$O$_2$; 341.2)<br>Calculated: C 49.28; H 4.14; N 16.42<br>Found: C 49.2 ; H 4.0 ; N 16.5 |

Product consists of approximately equal parts of an isomer mixture of
β-(2,6-dichlorophenyl)-β-(4,5,6,7-tetrahydrobenzotriazolyl-2)-nitroethane and
β-(2,6-dichlorophenyl)-β-(4,5,6,7-tetrahydrobenzotriazolyl-1)-nitroethane.

Table 3-continued

| Compound No. | Formula | Properties |
|---|---|---|
| 12 | (2,6-dichlorophenyl-CH(benzotriazolyl)-CH₂-NO₂) | Melting point 114 – 115°C |
| 13 | (2,6-dichlorophenyl-CH(benzopyrazolyl)-CH₂-NO₂) | Melting point 159 – 160°C |
| 14 | (2-trifluoromethylphenyl-CH(1,2,4-triazolyl)-CH₂-NO₂) | Melting point 84 – 85°C |

Other compounds which can be similarly prepared include:

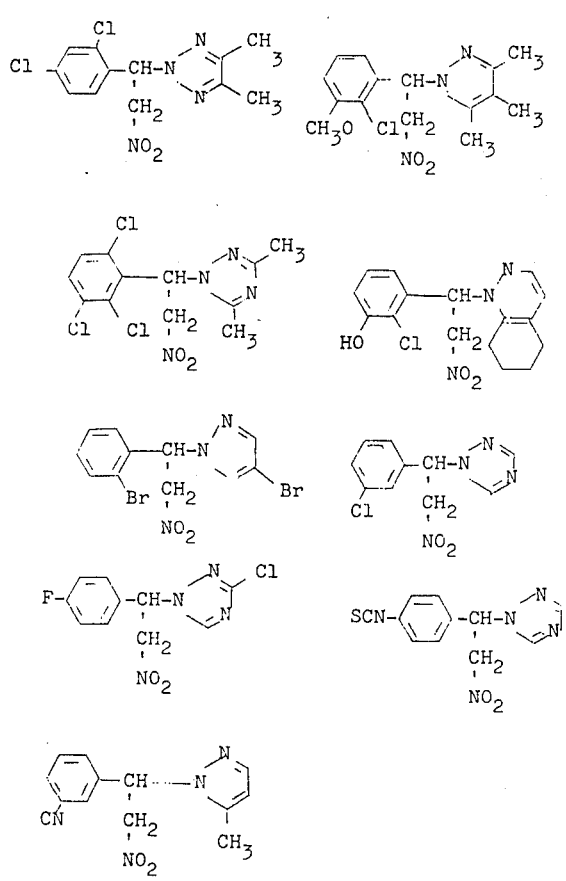

It will be appreciated that the instant specification and examples are set forth by way of illustration and not limitation, and that various modifications and changes may be made without departing from the spirit and scope of the present invention.

What is claimed is:

1. A β-phenyl-β-azolylnitroethane of the formula $$\begin{array}{c} R^1 \\ \text{(phenyl with } R^1, R^2, R^3\text{)} - CH - R^4 \\ | \\ CH_2 \\ | \\ NO_2 \end{array}$$

in which

R¹, R² and R³ each individually is hydrogen; methyl or ethyl optionally substituted by fluorine or chlorine; halogen; nitrile; thiocyano; nitro; or alkoxycarbonyl with up to 6 carbon atoms in the alkoxy radical, and R⁴ is a pyrazolyl-1, a benzopyrazolyl-1 or a tetrahydrobenzylpyrazolyl-1 radical optionally substituted on a carbon atom by halogen, methyl, ethyl, nitro or trifluoromethyl.

2. A compound according to claim 1, in which R¹, R² and R³ each individually is hydrogen, fluorine, chlorine, methoxycarbonyl, ethoxycarbonyl, or optionally chlorinated or fluorinated methyl or ethyl, and R⁴ is a pyrazolyl-1, a benzopyrazolyl-1 or a tetrahydrobenzopyrazolyl-1 radical optionally substituted on a carbon atom by methyl, ethyl, chlorine or fluorine.

3. A compound according to claim 1, in which R¹, R² and R³ each individually is hydrogen, chlorine or trifluoromethyl.

4. The compound according to claim 1 wherein such compound is β-(2,6-dichlorophenyl)-β-(pyrazolyl-1)-nitroethane of the formula

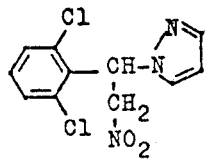

* * * * *